(12) United States Patent
Son et al.

(10) Patent No.: US 7,846,901 B2
(45) Date of Patent: Dec. 7, 2010

(54) METHOD FOR INHIBITING OR TREATING INTESTINAL DAMAGE CAUSED BY RADIOTHERAPY OR CHEMOTHERAPY COMPRISING ADMINISTERING SUBSTANCE-P

(75) Inventors: Young Sook Son, Seoul (KR); Do Yeon Kim, Gwangmyeong-si (KR); Hyun Sook Hong, Seoul (KR)

(73) Assignee: University-Industry Cooperation Group of Kyunghee University, Yongin-si (KR)

( * ) Notice: Subject to any disclaimer, the term of this patent is extended or adjusted under 35 U.S.C. 154(b) by 0 days.

(21) Appl. No.: 12/245,969

(22) Filed: Oct. 6, 2008

(65) Prior Publication Data

US 2009/0105154 A1     Apr. 23, 2009

(30) Foreign Application Priority Data

Oct. 5, 2007     (KR) ...................... 10-2007-0100469

(51) Int. Cl.
- *A61K 38/00* (2006.01)
- *A61K 38/03* (2006.01)
- *A61K 38/08* (2006.01)

(52) U.S. Cl. .......................... 514/15; 514/2

(58) Field of Classification Search ....................... None
See application file for complete search history.

(56) References Cited

U.S. PATENT DOCUMENTS

| | | | | |
|---|---|---|---|---|
| 3,608,064 A | * | 9/1971 | Lamb | 424/439 |
| 5,594,022 A | * | 1/1997 | Horwell et al. | 514/419 |
| 5,981,597 A | * | 11/1999 | Wu | 514/616 |
| 6,110,939 A | * | 8/2000 | Janssens et al. | 514/322 |
| 6,576,638 B1 | * | 6/2003 | Pompei et al. | 514/278 |
| 7,119,071 B2 | * | 10/2006 | Rameshwar | 514/18 |
| 7,745,403 B2 | * | 6/2010 | Larsen et al. | 514/12 |
| 2004/0214311 A1 | * | 10/2004 | Levy | 435/287.2 |
| 2006/0127373 A1 | * | 6/2006 | Son et al. | 424/93.7 |

OTHER PUBLICATIONS

Son et al. (2006, Mol. Biol. Cell 17 (Suppl.) L57).*
K. Bulut, et al.: "Sensory neuropeptides and epithelial cell restitution: the relevance of SP- and CGRP-stimulated mast cells," Int. J. Colorectal Dis., vol. 23, Feb. 15, 2008, pp. 535-541.
W.P. ter Beek, et al.: "Substance P receptor expression in patients with inflammatory bowel disease Determination by three different techniques, i.e., storage phosphor autoradiography, RT-PCR and immunohistochemistry," Neuropeptides, vol. 41, Jun. 28, 2007, pp. 301-306.
H. Koon, et al.: "Substance P mediates antiapoptotic responses in human colonocytes by Akt activation," PNAS, vol. 104, No. 6, Feb. 6, 2007, pp. 2013-2018.
J. Wang, et al.: "Calcitonin Gene-Related Peptide and Substance P Regulate the Intestinal Radiation Response," Clin Cancer Res, vol. 12(13), Jul. 1, 2006, pp. 4112-4118.
P. Felderbauer, et al.: "Substance P induces intestinal wound healing via fibroblasts—evidence for a TGF-β-dependent effect," Int. J. Colorectal Dis., vol. 22, May 23, 2007, pp. 1475-1480.
P. Felderbauer et al.: "Substance P induces intestinal wound healing via fibroblasts—evidence for a TGF-β-dependent effect," Int. J. Colorectal Dis. vol. 22, pp. 1475-1480, 2007.

* cited by examiner

*Primary Examiner*—Elizabeth C Kemmerer
(74) *Attorney, Agent, or Firm*—Rothwell, Figg, Ernst & Manbeck, P.C.

(57) ABSTRACT

Disclosed herein are a composition for prevention or treatment of gastrointestinal damage comprising Substance-P as an active ingredient, a use of Substance-P for the preparation of a medicament for prevention or treatment of gastrointestinal damage, and a method for prevention or treatment of gastrointestinal damage comprising administering a therapeutically effective amount of Substance-P to a mammal.

2 Claims, 4 Drawing Sheets

Unirradiated control 4.5h post-irradiation 1 days post-irradiation 4.5h post-irradiation
(Substance-P injection)

1 days post-irradiation
(Substance-P injection)

METHOD FOR INHIBITING OR TREATING INTESTINAL DAMAGE CAUSED BY RADIOTHERAPY OR CHEMOTHERAPY COMPRISING ADMINISTERING SUBSTANCE-P

TECHNICAL FIELD

The present invention relates to a composition for prevention or treatment of gastrointestinal damage comprising Substance-P as an active ingredient, a use of Substance-P for the preparation of a medicament for prevention or treatment of gastrointestinal damage, and a method for prevention or treatment of gastrointestinal damage comprising administering a therapeutically effective amount of Substance-P to a mammal.

BACKGROUND ART

Substance-P (SP) is an 11-amino acid neuropeptide which is expressed in sensory neurons, macrophages, eosinophils, endothelial cells, and corneal cells such as epithelial cells and keratocytes as well as granulation tissues.

The present inventors found through a previous study that Substance-P can facilitate mobilization and repopulation of mesenchymal stem cells (MSCs) to thereby accelerate wound healing (Korean Patent No. 10-593397). In a subsequent study, the present inventors also discovered that Substance-P is capable of exerting therapeutic effects on bone marrow damage through stimulation of the mesenchymal stem cell repopulation to thereby facilitate proliferation of bone marrow cells and hematopoietic stem cells, in bone marrow damage with accompanying cellular destruction of bone marrow cells and hematopoietic stem cells (Korean Patent No. 10-2007-0006409).

DISCLOSURE OF THE INVENTION

Technical Problem

Therefore, the present invention has been made in view of the above problems, and it is an object of the present invention to provide a composition for prevention or treatment of gastrointestinal damage comprising Substance-P as an active ingredient.

It is another object of the present invention to provide a use of Substance-P for the preparation of a medicament for prevention or treatment of gastrointestinal damage.

It is a further object of the present invention to provide a method for prevention or treatment of gastrointestinal damage comprising administering a therapeutically effective amount of Substance-P to a mammal.

Technical Solution

The present invention provides a composition for prevention or treatment of gastrointestinal damage comprising Substance-P as an active ingredient; a use of Substance-P for the preparation of a medicament for prevention or treatment of gastrointestinal damage; and a method for prevention or treatment of gastrointestinal damage comprising administering a therapeutically effective amount of Substance-P to a mammal.

Hereinafter, the present invention will be described in more detail.

The present invention provides a composition for prevention or treatment of gastrointestinal damage comprising Substance-P as an active ingredient.

In order to demonstrate prophylactic and therapeutic effects of Substance-P on gastrointestinal damage, gastrointestinal damage was radiation-induced in mice. Then, crypt cell apoptosis and regeneration and villous damage and repair were observed and compared between the Substance-P administered group and the non-treated group. As a result, it was confirmed that the Substance-P administered group exhibits significantly lower apoptotic rate of crypt cells and faster recovery of damaged crypt cells and villi to a normal state, as compared to the non-treated control group.

Therefore, it is possible to achieve treatment of gastrointestinal damage as well as effective prevention of gastrointestinal damage, when the composition of the present invention comprising Substance-P as an active ingredient is therapeutically used for gastrointestinal damage.

The pharmaceutical composition of the present invention may further comprise pharmaceutically and physiologically acceptable additives, in addition to the active ingredient. Examples of such additives may include excipients, disintegrants, sweeteners, binders, coating agents, blowing agents, lubricants, glidants, flavoring agents, solubilizers, etc.

The composition of the present invention may further comprise one or more pharmaceutically acceptable carriers besides the active ingredient, to be formulated into a pharmaceutical composition appropriately.

Dosage forms of the composition of the present invention may include granules, powders, tablets, coated tablets, capsules, suppositories, enemas, syrups, juice, suspensions, emulsions, and injectable liquid formulations.

For formulation of the composition into a tablet or capsule, the active ingredient may be combined with any oral, non-toxic and pharmaceutically acceptable inert carrier, such as ethanol, glycerol, water, etc. If desired or necessary, suitable binders, lubricants, disintegrants and colorants may be additionally added to the composition. Examples of the suitable binder may include, but are not limited to, starch, gelatin, natural sugars such as glucose and beta-lactose, corn sweeteners, natural and synthetic gums such as acacia, tragacanth and sodium oleate, sodium stearate, magnesium stearate, sodium benzoate, sodium acetate, sodium chloride and the like. Examples of the disintegrant may include, but are not limited to, starch, methyl cellulose, agar, bentonite, and xanthan gum.

For formulation of the composition into a liquid preparation, a pharmaceutically acceptable carrier which is sterile and biocompatible may be used such as saline, sterile water, Ringer's solution, buffered physiological saline, albumin infusion solution, dextrose solution, maltodextrin solution, glycerol, and ethanol. These materials may be used alone or in any combination thereof. If necessary, other conventional additives may be added such as antioxidants, buffers, bacteriostatic agents, and the like. Further, diluents, dispersants, surfactants, binders and lubricants may be additionally added to the composition to prepare injectable formulations such as aqueous solutions, suspensions, and emulsions, or oral formulations such as pills, capsules, granules, and tablets. Furthermore, the composition may be preferably formulated into a desired dosage form, depending upon diseases to be treated and ingredients, using any appropriate method known in the art, as disclosed in "Remington's Pharmaceutical Sciences," Mack Publishing Co., Easton, Pa.

The composition of the present invention may further comprise one or more therapeutic drugs for gastrointestinal damage. For example, Substance-P may be used in combination with therapeutic drugs for gastritis, gastric ulcers, duodenal ulcers, etc. which are well known to those skilled in the art.

Further, the present invention provides a use of Substance-P for the preparation of a medicament for prevention or treatment of gastrointestinal damage.

The pharmaceutical composition containing Substance-P may be used for the preparation of such a gastrointestinal drug.

Further, the present invention provides a method for prevention or treatment of gastrointestinal damage comprising administering a therapeutically effective amount of Substance-P to a mammal.

In the context of the present invention, treatment of gastrointestinal damage is intended to include alleviation of gastrointestinal damage.

In the context of the present invention, the gastrointestinal damage is intended to encompass gastrointestinal injuries that may be caused by various pathogenic factors such as irradiation (radiotherapy), anticancer drug administration (chemotherapy), and the like.

When the occurrence of gastrointestinal damage is inevitable due to radiotherapy or chemotherapy, for example, pretreatment of a subject with Substance-P prior to application of such an anticancer therapy can lead to significant reduction in the extent of gastrointestinal damage. Further, administration of Substance-P in combination with conventional anticancer therapy can prevent severe gastrointestinal damage that may occur due to the anticancer therapy, which then enables prevention, treatment or alleviation of attendant side effects of anticancer regimens, i.e. gastrointestinal damage.

Consequently, prevention, treatment or alleviation of gastrointestinal damage resulting from conventional anticancer therapy can be accomplished via administration of the composition or medicament for prevention or treatment of gastrointestinal damage according to the present invention, concurrently with, before or after radiotherapy or chemotherapy.

Further, the present invention provides a method for prevention or treatment of gastrointestinal damage comprising administering a therapeutically effective amount of Substance-P to a mammal.

The present invention also provides a method for prevention or treatment of gastrointestinal damage which is caused by radiotherapy or chemotherapy comprising administering a therapeutically effective amount of Substance-P to mammal.

According to the present invention, said administering step can be done concurrently with, before or after radiotherapy or chemotherapy.

The pharmaceutical composition of the present invention comprising Substance-P as an active ingredient may be administered via a conventional route, for example intravenously, intraarterially, intraperitoneally, intramuscularly, intrathoracically, percutaneously, intranasally, locally, rectally, orally, intraocularly, intradermally, or by inhalation.

As used herein, the term "mammal" refers to any mammalian species that is in need of treatment, examination or experiment, preferably human.

As used herein, the term "therapeutically effective amount" refers to an amount of an active ingredient or pharmaceutical composition that will elicit the biological or medical response of a tissue system, animal or human that is being sought by a researcher, veterinarian, medical practitioner or clinician, and encompasses an amount of the active ingredient or pharmaceutical composition which will ameliorate the symptoms of the disease or disorder being treated. As will be apparent to those skilled in the art, the therapeutically effective dose and administration times of the active ingredient in accordance with the present invention may vary depending upon desired therapeutic effects. Therefore, an optimal dose of the active drug to be administered can be easily determined by those skilled in the art. For example, an effective dose of the drug is determined taking into consideration various factors such as kinds of disease, severity of disease, contents of active ingredients and other components contained in the composition, kinds of formulations, age, weight, general health status, sex and dietary habits of patients, administration times and routes, release rates of the composition, treatment duration, and co-administered drugs.

In the present invention, an effective dose (ED) of Substance-P may be in a range of around 0.1 to 100 µg/kg/day.

Substance-P prevents apoptosis of gastrointestinal cells and promotes regeneration of damaged tissues. Therefore, the composition of the present invention comprising Substance-P as an active ingredient is therapeutically effective for treatment and/or prevention of gastrointestinal damage.

ADVANTAGEOUS EFFECTS

As described hereinbefore, Substance-P prevents apoptosis (or cell death) of gastrointestinal cells and promotes regeneration of damaged tissues. Therefore, the composition of the present invention comprising Substance-P as an active ingredient is therapeutically effective for treatment and/or prevention of gastrointestinal damage.

MODE FOR INVENTION

Figure 1:
FIG. 1 is a photograph showing TUNEL assay results for apoptosis of crypt cells, taken 4.5 hours and 1 day after exposure of mice to radiation.
Figure 1:
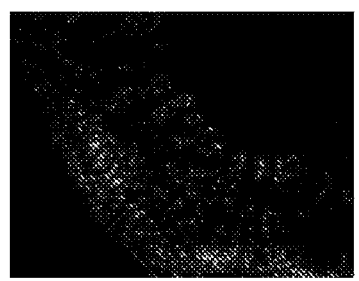
Figure 1:
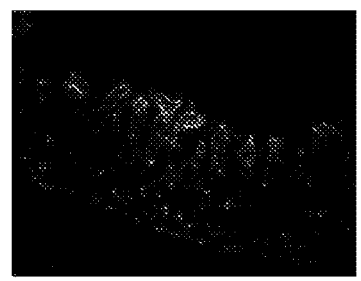
Figure 1:
Figure 1:
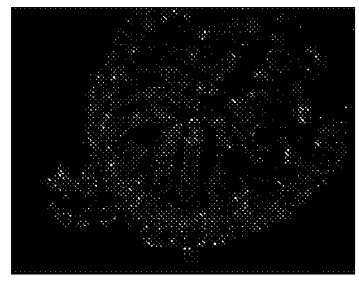

These and other objects, advantages and features of the present invention will become apparent from the detailed embodiments given below which are made in conjunction with the following Examples. The present invention may be embodied in different forms and should not be misconstrued as being limited to the embodiments set forth herein, and those skilled in the art will appreciate that various modifications, additions and substitutions are possible without departing from the scope and spirit of the invention as disclosed in the accompanying claims. Therefore, it should be understood that the embodiments disclosed herein are provided only for illustrating the present invention and should not be construed as limiting the scope and spirit of the present invention.

EXAMPLE 1

Gastrointestinal Protective and Therapeutic Effects of Substance-P (1) Administration of Substance-P to Gastrointestinal Lesions and Construction of Tissue Section Slide 8-week-old C57bl/6 mice (Central Lab Animal Inc., Seoul, Korea) were irradiated with gamma rays to establish an animal model of gastrointestinal damage, and gastrointestinal protective and regenerative effects of Substance-P were then examined.

For this purpose, C57b1/6 mice were divided into two groups, an experimental group and a control group, each consisting of 5 animals (n=5). 100 nM of Substance-P (Cat. No. 05-23-0600, Calbiochem) was injected to the experimental group mice via tail vein, 24 hours prior to gamma ray irradiation. 24 hours later, animals were irradiated with a gamma irradiator at a dose of 7.6 Gy. Immediately after gamma ray irradiation, 100 nM of Substance-P was intravenously injected once more into animals of the experimental group. The control group was given PBS.

4.5 hours, 3 days, and 7 days later, mice of each group were euthanized by $CO_2$ asphyxiation and then received abdominal incision. Small intestines were isolated and fixed in a 3.7% formaldehyde solution for tissue fixation, for 1 to 2 days. Following the tissue processing process, the tissues were hardened in a paraffin block. The formalin-fixed paraffin tissues were sectioned to a 5 μm thickness using a microtome and then attached to a coated slide glass which was then dried, followed by TUNEL staining, Brd-U immunostaining and H&E staining. For Brd-U immunostaining, 2 hours prior to sacrifice of mice, 50 mg/kg of 5-bromo-2-deoxyuridine (Brd-U, Cat. No. B-9285, Sigma) was introduced into dividing cells by peritoneal injection.

(2) Anti-Apoptotic Effects of Substance-P

Dead cells were detected by fluorescence labeling of damaged DNA molecules through TUNEL assay using an In Situ Cell Death Detection Kit (Cat. No. 1 684 795, Roche Molecular Biochemicals).

The tissue section slide was deparaffinized with xylene and hydrated in alcohol. The tissue section was treated with 0.1% Triton X-100 (Cat. No. 22686, USB Corp.) for 2 min to increase cell permeability. Then, a TUNEL reaction mixture of a label solution and an enzyme solution was treated on the tissue section slide, followed by reaction at 37° C. for 60 min. Nuclear staining was carried out using 4',6-diamidino-2-phenylindole (DAPI, Cat. No. D-9542, Sigma) and the stained tissue was examined in a green field of 515 to 565 nm under a fluorescence microscope.

When gamma rays at a dose of 7.6 Gy were systemically irradiated to animals, gastrointestinal cells were rapidly damaged. As shown in FIG. 1, the control group without administration of Substance-P exhibited death of crypt cells at the site which is putatively thought to be a stem cell zone, 4.5 hours after gamma ray irradiation. One day later, overall death of crypt cells was observed due to the gamma ray irradiation. The group with administration of Substance-P one day prior to gamma-ray exposure exhibited significant reduction in apoptosis of crypt stem cells that occurs at the time point of 4.5 hours after exposure of animals to gamma rays.

(3) Proliferative Effects of Substance-P on Crypt Cells

Proliferative effects of Substance-P on crypt cells were examined by Brd-U immunohistochemical staining.

The tissue section slide was deparaffinized with xylene and hydrated in alcohol. The tissue section was pretreated with 2N HCl for 30 min, and endogenous peroxidase activity was blocked with addition of $H_2O_2$ for 10 min. The tissue section was treated with 0.3% Triton X-100 for 5 min to increase cell permeability. Then, 2% serum in a Vector ABC kit (PK-6100, Vector Laboratories Inc.) was added to block the cells. BrdU antibodies (Cat. No. 1 170 376, Roche Molecular Biochemicals) and 2% serum were diluted in a ratio of 6:100, followed by reaction at room temperature for 1 hour. This was followed by reaction with biotinylated-secondary antibodies (Cat. No. PK-6100, Vector Laboratories Inc.). Then, the reaction was amplified with addition of streptavidin-peroxidase (Cat. No. PK-6100, Vector Laboratories Inc.) and the reaction product was treated with a DAB solution (Cat. No. SK-4100, Vector Laboratories Inc.), followed by examination.

Figure 2:
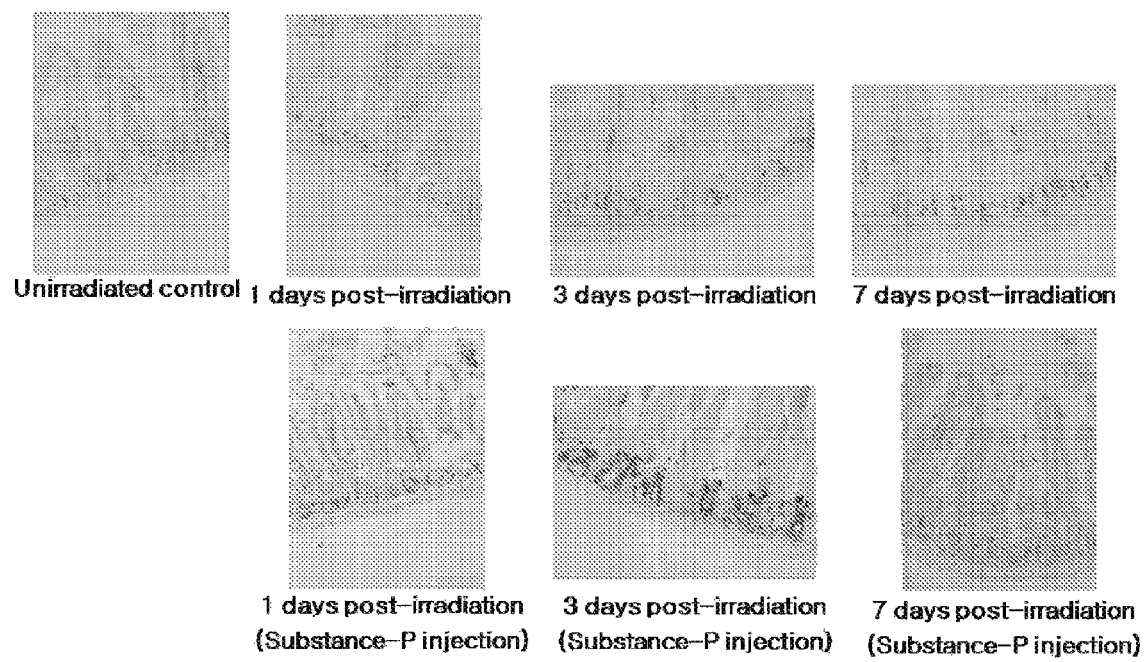
FIG. 2 is a photograph of BrdU staining patterns showing hyperplasia (overproliferation) of crypt cells, taken on Days 1, 3 and 7 after exposure of mice to radiation.

As shown in FIG. 2, when the cells were observed with BrdU staining which is used for staining of dividing cells, there was no significant difference in staining of cells on Day 1 of gamma ray irradiation, irrespective of whether Substance-P was administered or not. On Day 3, mice with injection of Substance-P exhibited intense staining in large numbers of cells. Crypt hyperplasia for the recovery from gastrointestinal damage after it occurred was actively observed from 3 to 5 days after exposure of animals to gamma ray irradiation. From the results of FIG. 2, it appears that administration of Substance-P results in earlier gastrointestinal recovery through crypt hyperplasia. On Day 7, the number of dividing crypt cells and the crypt size in mice with administration of Substance-P were similar to those of the non-irradiated control group, whereas mice without administration of Substance-P exhibited a large number of dividing crypt cells and a large size of the crypt, thus implying that complete recovery from gastrointestinal damage was not achieved to a normal state. In conclusion, administration of Substance-P appears to bring earlier gastrointestinal recovery.

(4) Observation of Changes in Crypt Cell Survival Rate and Villous Height

After the tissue section slide was H&E-stained and photographed, crypt cell counts and villous heights were measured and averaged, respectively.

2 to 3 days after exposure of experimental animals to radiation, villous atrophy occurred due to death of crypt cells and simultaneously crypt hyperplasia initiated in other regions and continued for about 5 days. The crypt which became excessively larger than a normal size exhibited increased numbers of crypt cells through crypt branching, thus resulting in recovery of the number of crypt cells to a normal level.

Figure 3:
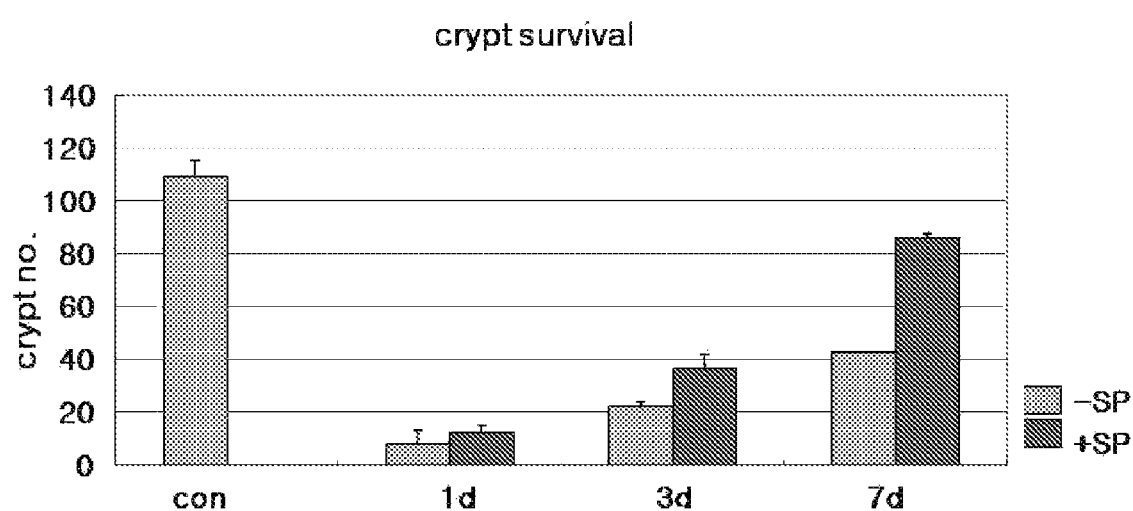
FIG. 3 is a graph showing survival of crypt cells on Days 1, 3 and 7 after exposure of mice to radiation.
Figure 4:
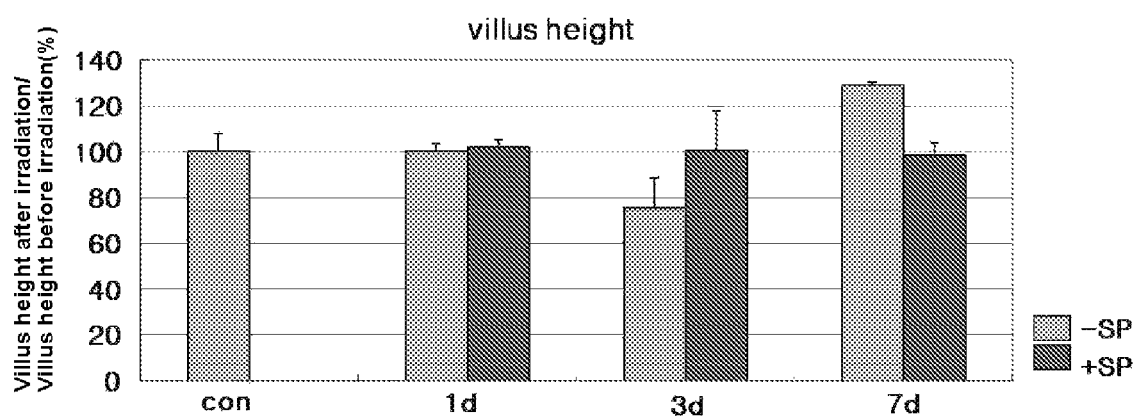
FIG. 4 is a graph of BrdU staining patterns showing villous height on Days 1, 3 and 7 after exposure of mice to radiation.

As shown in FIG. 3, viable crypt cells were counted to confirm that the mouse group with administration of Substance-P exhibited a higher number of viable crypt cells. Further, as shown in FIG. 4, it was confirmed that when a villous height was measured at different time points, the group with administration of Substance-P exhibited less villous atrophy on Day 3, and the group with administration of Substance-P exhibited a villous height similar to that of a non-irradiated normal control group, on Day 7.

With revival of crypt cells, atrophied villi became a normal size or larger, then returned to normal height and morphology and finally reached a normal state around Day 7 or 8. When Substance-P was previously injected into radiation-damaged small intestinal cells, it was observed that apoptosis of stem cells is decreased and a recovery time from gastrointestinal damage is also shortened.

What is claimed is:

1. A method for inhibiting or treating damage to the small or large intestine, comprising administering to a mammal Substance P in an amount effective for inhibiting or treating the damage; and then subjecting the mammal to radiotherapy or chemotherapy, wherein the damage to the large or small intestine is caused by radiotherapy or chemotherapy.

2. A method for reducing damage to the small or large intestine, comprising administering to a mammal Substance P in an amount effective for inhibiting or treating the damage; and then
    subjecting the mammal to radiotherapy or chemotherapy, wherein the damage to the large or small intestine is caused by radiotherapy or chemotherapy.

* * * * *